United States Patent [19]

Kurz

[11] Patent Number: 4,512,740
[45] Date of Patent: Apr. 23, 1985

[54] PLASTIC SHIELD FOR ORTHODONTIC APPLIANCE

[76] Inventor: Craven H. Kurz, 465 N. Roxbury Dr., #1011, Beverly Hills, Calif. 90210

[21] Appl. No.: 587,220

[22] Filed: Mar. 7, 1984

[51] Int. Cl.³ .............................................. A61C 7/00
[52] U.S. Cl. .......................................... 433/22; 433/6; 433/8
[58] Field of Search ............................ 433/6, 8, 14, 22

[56] References Cited

U.S. PATENT DOCUMENTS 3,319,626  5/1967  Lindsay ................................. 433/6
4,180,912  1/1980  Kesling ................................ 433/14

Primary Examiner—Robert Peshock
Attorney, Agent, or Firm—Keith D. Beecher

[57] ABSTRACT

A plastic shield for preventing irritation to the inner tissue of the cheeks and lips of a patient when a labial orthodontic appliance is in place, and which prevents irritation to the tongue of a patient when a lingual appliance is in place. The shield of the appliance covering the orthodontic attachments to provide a smooth outer surface.

2 Claims, 4 Drawing Figures

PLASTIC SHIELD FOR ORTHODONTIC APPLIANCE

BACKGROUND OF THE INVENTION

It has long been the orthodontic practice to attach the orthodontic appliance to the labial side of the patient's teeth. However, U.S. Pat. Nos. 4,107,844 and 4,386,908 which issued to the present inventor, describe orthodontic appliances which are attached to the lingual side of the patient's teeth to be hidden from view.

The orthodontic appliances in either instance can be a source of irritation and trauma to the patient, either to the lips and cheeks in the case of the labial appliance, or to the tongue in the case of the lingual appliance.

The purpose and objective of the present invention is to provide a plastic shield which may be fitted over the attachments, ligatures and arch wires of the aforesaid appliances to present a smooth outer surface and obviate irritation to the tongue in the case of the lingual appliances, and to obviate irritation to the inner tissue of the cheeks and lips in the case of the labial appliances.

In general, the principal objective of the present invention is to provide an orthodontic shield which serves to protect the labial or lingual oral tissue from irritation from a labial or lingual orthodontic appliance, when such an appliance has been fitted onto the teeth of a patient.

DETAILED DESCRIPTION OF THE ILLUSTRATED EMBODIMENT

Figure 1:
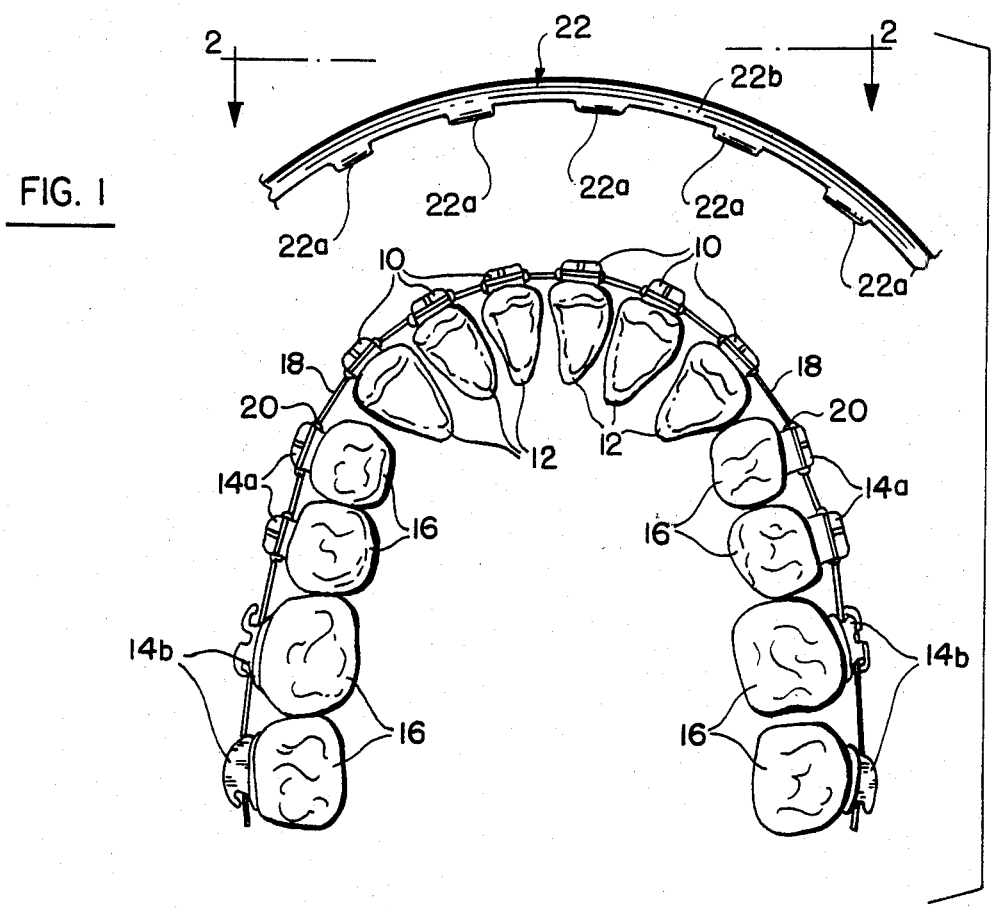
FIG. 1 is a representation of a prior art labial orthodontic appliance system, and also shows a portion of a plastic shield which, in accordance with the concepts of the present invention may be fitted over the appliance.

The labial orthodontic appliance of FIG. 1 includes a number of brackets 10 which are bonded to the labial surfaces of the anterior teeth of the patient designated generally as 12, and a number of brackets and tubes designated collectively as 14a and 14b which are bonded to the labial surfaces of the posterior teeth of the patient designated collectively as 16.

An arch wire 18 extends through the brackets and tubes 10 and 14 around the arch, and the arch wire 18 is secured to the brackets and tubes by appropriate ligatures designated 20.

Under normal circumstances when the appliance of FIG. 1 is fitted into the mouth of a patient, trauma can occur to the lips and cheeks of the patient due to irritation created by the brackets 10, tubes 14, arch wire 18, and the ligatures 20.

Figure 2:
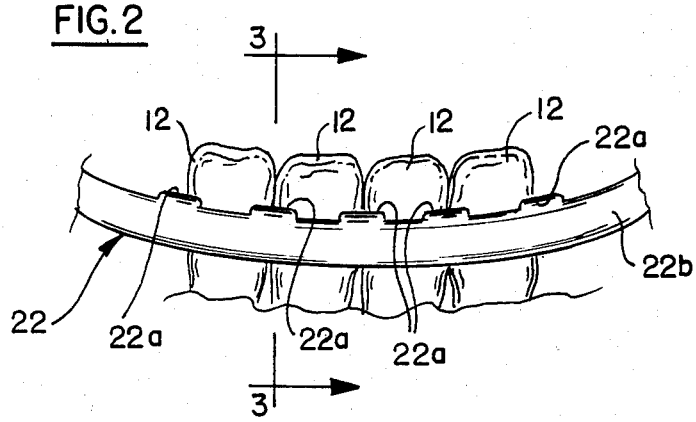
FIG. 2 is a view of the shield of FIG. 1 taken along the line 2—2 of FIG. 1.
Figure 3:
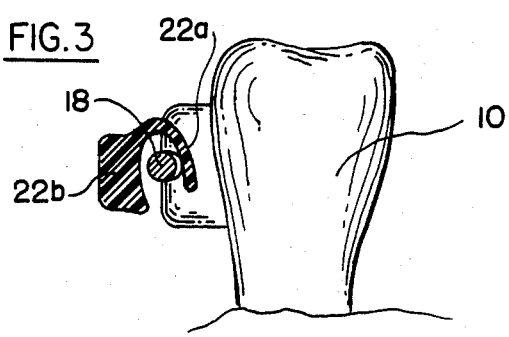
FIG. 3 is a cross-sectional view taken essentially along the line 3—3 of FIG. 2.

The present invention provides a plastic shield 22 which has a smooth outer surface, as shown in FIG. 2, and which comprises a number of fingers 22a which are integral with a band 22b. The fingers 22a extend around the arch wire 18, such as shown in FIG. 3, to hold the shield in place. For extra security, dental floss may be threaded between the interproximal spaces of the teeth and tied to the shield 22 to secure the shield to the teeth.

The shield 22, accordingly, serves to reduce trauma to the lips and cheeks of the patient wearing the orthodontic appliance of FIG. 1.

Figure 4:
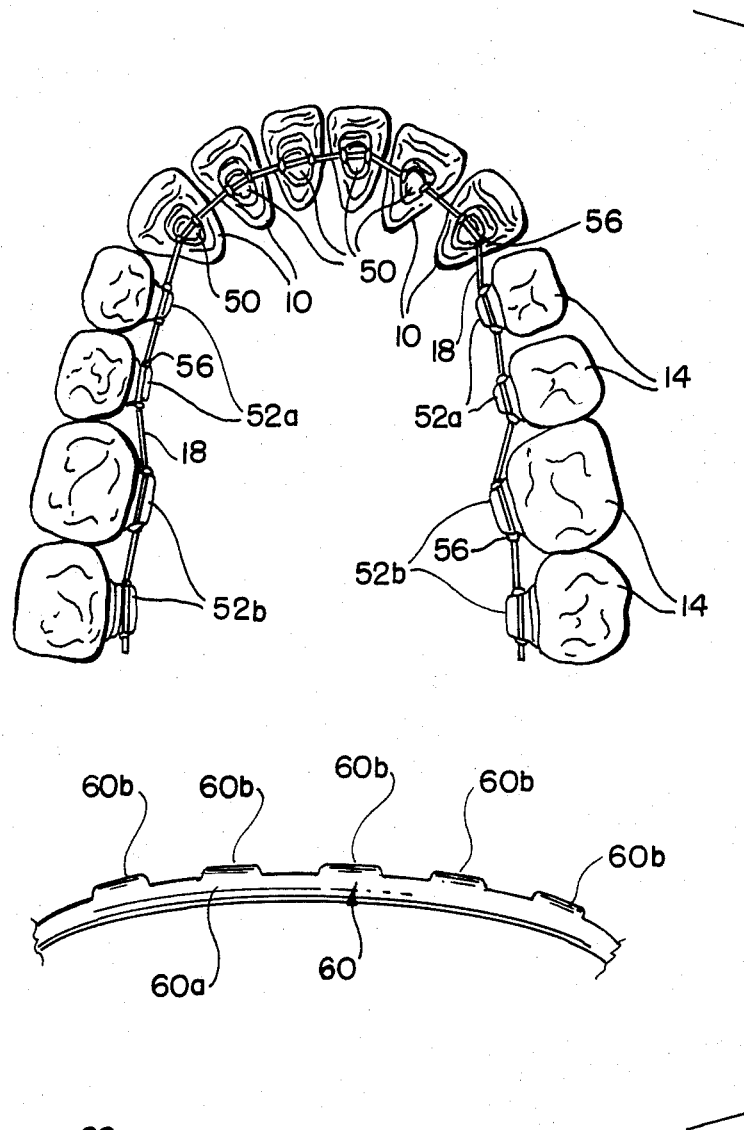
FIG. 4 is a representation of a lingual orthodontic appliance system of the general type described in the Kurz patent referred to above; and also of a plastic shield constructed particularly to fit over the elements of the lingual appliance of FIG. 4.

In the representation of FIG. 4, a lingual appliance is fitted onto the lingual side of the arch. The lingual appliance includes a number of brackets 50 which are bonded to the lingual side of the anterior teeth 10, and a number of brackets and tubes 52a and 52b which are bonded to the lingual side of the posterior teeth. An arch wire 54 extends around the lingual side of the arch through the brackets and tubes, the arch wire being secured to the brackets and tubes, for example, by ligatures 56.

In accordance with the invention, a particular shield 60 is provided which fits over the brackets 50, for example, of the appliance of FIG. 4. The shield 60, like the shield 22 of FIG. 1, includes a band 60a which provides a smooth inner surface, and which includes a number of inner fingers 60b which fit over the arch wire 18 to support the shield on the teeth, with the shield covering the brackets 50, arch wire 18, and ligatures 56. As before, the shield 60 may also be tied by dental floss as an assurance that it will remain in place over the elements of the lingual appliance.

The invention provides, therefore, a plastic shield which may conveniently be fitted over a labial or lingual orthodontic appliance, so as to protect the oral tissue of the patient from irritation due to the elements of the appliance.

It will be appreciated that while a particular embodiment of the invention has been shown and described, modifications may be made. It is intended in the claims to cover all modifications which come within the true spirit and scope of the invention.

What is claimed is:

1. A shield for an orthodontic appliance to protect the oral tissue of a patient from irritation when the patient is wearing the appliance, the appliance comprising a plurality of orthodontic attachments and an arch wire extending between the attachments, and a shield comprising an elongated arcuate member having a smooth outer face, and a plurality of fingers integral with said member and extending around the arch wire to engage the arch wire and hold the member in place covering the attachments of the appliance.

2. The shield defined in claim 1, in which the member is formed of a plastic material.

* * * * *